(12) United States Patent
Yoshinaga et al.

(10) Patent No.: US 12,178,393 B2
(45) Date of Patent: Dec. 31, 2024

(54) PLUG, CONNECTOR, ENDOSCOPE APPARATUS, AND ENDOSCOPE

(71) Applicant: OLYMPUS CORPORATION, Tokyo (JP)

(72) Inventors: Takuto Yoshinaga, Hino (JP); Kazuma Kaneko, Hachioji (JP); Masanori Sumiyoshi, Hachioji (JP); Tsukasa Ota, Hachioji (JP); Wataru Matsuura, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 538 days.

(21) Appl. No.: 17/542,950

(22) Filed: Dec. 6, 2021

(65) Prior Publication Data

US 2022/0087510 A1  Mar. 24, 2022

Related U.S. Application Data

(63) Continuation of application No. PCT/JP2019/023559, filed on Jun. 13, 2019.

(51) Int. Cl.
*A61B 1/00* (2006.01)

(52) U.S. Cl.
CPC ...... *A61B 1/00121* (2013.01); *A61B 1/00124* (2013.01); *A61B 1/00126* (2013.01)

(58) Field of Classification Search
CPC .............. A61B 1/00126; G02B 6/3825; G02B 6/3885; G02B 6/3893; G02B 6/4292
See application file for complete search history.

(56) References Cited

U.S. PATENT DOCUMENTS

| 2003/0077043 | A1 | 4/2003 | Hamm et al. |
| 2008/0039693 | A1 | 2/2008 | Karasawa |
| 2011/0184244 | A1* | 7/2011 | Kagaya .............. A61B 1/00117 600/182 |

(Continued)

FOREIGN PATENT DOCUMENTS

| JP | H06-040915 U | 5/1994 |
| JP | 2005-533533 A | 11/2005 |

(Continued)

OTHER PUBLICATIONS

International Search Report dated Sep. 3, 2019 received in PCT/JP2019/023559.
English abstract only of US 2016/183771 A1.

*Primary Examiner* — Aaron B Fairchild
(74) *Attorney, Agent, or Firm* — Scully, Scott, Murphy & Presser, P.C.

(57) ABSTRACT

A plug of a connector for connecting an optical waveguide provided in a medical instrument includes: a coupling portion configured to be inserted into a receptacle of the connector; a connecting surface formed at an end in a first direction in which the coupling portion is inserted into the receptacle; an opening portion provided on the connecting surface, the opening portion having a recessed shape; and a holding portion configured to hold the optical waveguide such that an end face of the optical waveguide is directed in the first direction. The holding portion and the optical waveguide are disposed on a side of a second direction with respect to the connecting surface, the second direction being opposite to the first direction.

20 Claims, 8 Drawing Sheets

(56) References Cited

U.S. PATENT DOCUMENTS

2012/0002928 A1* 1/2012 Irisawa ................ G02B 6/3851
385/92
2017/0153439 A1* 6/2017 Horiike ................ A61B 8/4483

FOREIGN PATENT DOCUMENTS

| JP | 2006-204605 A | 8/2006 |
| JP | 2008-043763 A | 2/2008 |
| JP | 2010-131192 A | 6/2010 |
| JP | 2015-177902 A | 10/2015 |
| JP | 2017-023605 A | 2/2017 |
| JP | 2018-500995 A | 1/2018 |
| WO | 2003/088826 A1 | 10/2003 |

* cited by examiner

PLUG, CONNECTOR, ENDOSCOPE APPARATUS, AND ENDOSCOPE

CROSS-REFERENCE TO RELATED APPLICATION

This application is a continuation application of PCT/JP2019/023559 filed on Jun. 13, 2019, the entire contents of which are incorporated herein by this reference.

BACKGROUND OF THE INVENTION

1. Field of the Invention

The present invention relates to a plug configured to connect an optical waveguide of an endoscope, a connector, an endoscope apparatus, and an endoscope.

2. Description of the Related Art

As disclosed in Japanese Patent Application Laid-Open Publication No. 2010-131192, for example, an endoscope, when being in use, is connected to a processor through a connector. The endoscope is provided with a plug configured to be inserted into a receptacle provided to a processor. The plug and the receptacle, when connected to each other, transmit illumination light emitted from a light source apparatus to the endoscope, and transmit power and signals between the endoscope and the processor. In the state where the plug and the receptacle are connected to each other, the illumination light is incident on an optical waveguide such as an optical fiber provided in the endoscope.

SUMMARY OF THE INVENTION

A plug according to one aspect of the present invention is a plug of a connector for connecting one or a plurality of optical waveguides provided in a medical instrument. The plug includes: a coupling portion configured to be inserted into a receptacle of the connector; a connecting surface formed at an end in a first direction of the coupling portion, the first direction being a direction in which the coupling portion is inserted into the receptacle; an opening portion provided on the connecting surface, the opening portion having a recessed shape; and a holding portion disposed in the opening portion, the holding portion being configured to hold the one or the plurality of optical waveguides such that an end face of each of the one or the plurality of optical waveguides is directed in the first direction. The holding portion and the one or the plurality of optical waveguides are disposed on a side of a second direction with respect to the connecting surface, the second direction being opposite to the first direction.

A connector according to one aspect of the present invention is a connector for connecting one or a plurality of optical waveguides provided in a medical instrument. The connector includes a receptacle and a plug. The plug includes: a coupling portion configured to be inserted into the receptacle; a connecting surface formed at an end in a first direction of the coupling portion, the first direction being a direction in which the coupling portion is inserted into the receptacle; an opening portion provided on the connecting surface, the opening portion having a recessed shape; and a holding portion disposed in the opening portion, the holding portion being configured to hold the one or the plurality of optical waveguides such that an end face of each of the one or the plurality of optical waveguides is directed in the first direction. The holding portion and the one or the plurality of optical waveguides are disposed on a side of a second direction with respect to the connecting surface, the second direction being opposite to the first direction. The receptacle includes a recessed portion in which the coupling portion is inserted.

An endoscope apparatus according to one aspect of the present invention is an endoscope apparatus that includes an endoscope including a plug, and an endoscope processor including a receptacle, and that is configured such that one or a plurality of optical waveguides provided in the endoscope are connected in a state where the plug is inserted into the receptacle. The endoscope includes the plug including: a coupling portion configured to be inserted into the receptacle; a connecting surface formed at an end in a first direction of the coupling portion, the first direction being a direction in which the coupling portion is inserted into the receptacle; an opening portion provided on the connecting surface, the opening portion having a recessed shape; and a holding portion disposed in the opening portion, the holding portion being configured to hold the one or the plurality of optical waveguides such that an end face of each of the one or the plurality of optical waveguides is directed in the first direction. The holding portion and the one or the plurality of optical waveguides are disposed on a side of a second direction with respect to the connecting surface, the second direction being opposite to the first direction. The endoscope processor includes: the receptacle including a recessed portion in which the coupling portion is inserted, and one or a plurality of emission holes, each being formed at a position opposing to the end face of each of the one or the plurality of optical waveguides in a state where the coupling portion is fitted in the recessed portion; and a light source apparatus configured to emit light toward the one or the plurality of emission holes in the state where the coupling portion is fitted in the recessed portion.

An endoscope according to one aspect of the present invention is an endoscope including a plug of a connector for connecting one or a plurality of optical waveguides. The plug includes: a coupling portion configured to be inserted into a receptacle of the connector; a connecting surface formed at an end in a first direction of the coupling portion, the first direction being a direction in which the coupling portion is inserted into the receptacle; an opening portion provided on the connecting surface, the opening portion having a recessed shape; and a holding portion disposed in the opening portion, the holding portion being configured to hold the one or the plurality of optical waveguides such that an end face of each of the one or the plurality of optical waveguides is directed in the first direction. The holding portion and the one or the plurality of optical waveguides are disposed on a side of a second direction with respect to the connecting surface, the second direction being opposite to the first direction.

DETAILED DESCRIPTION OF THE PREFERRED EMBODIMENT(S)

Figure 1:
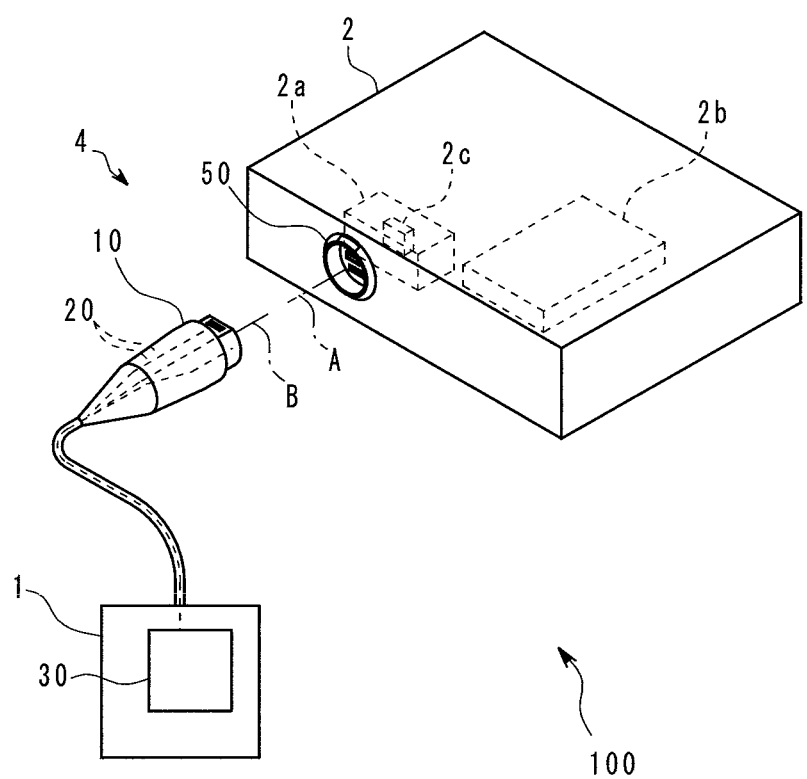
FIG. 1 is a view showing a schematic configuration of an endoscope apparatus including a connector.
Figure 2:
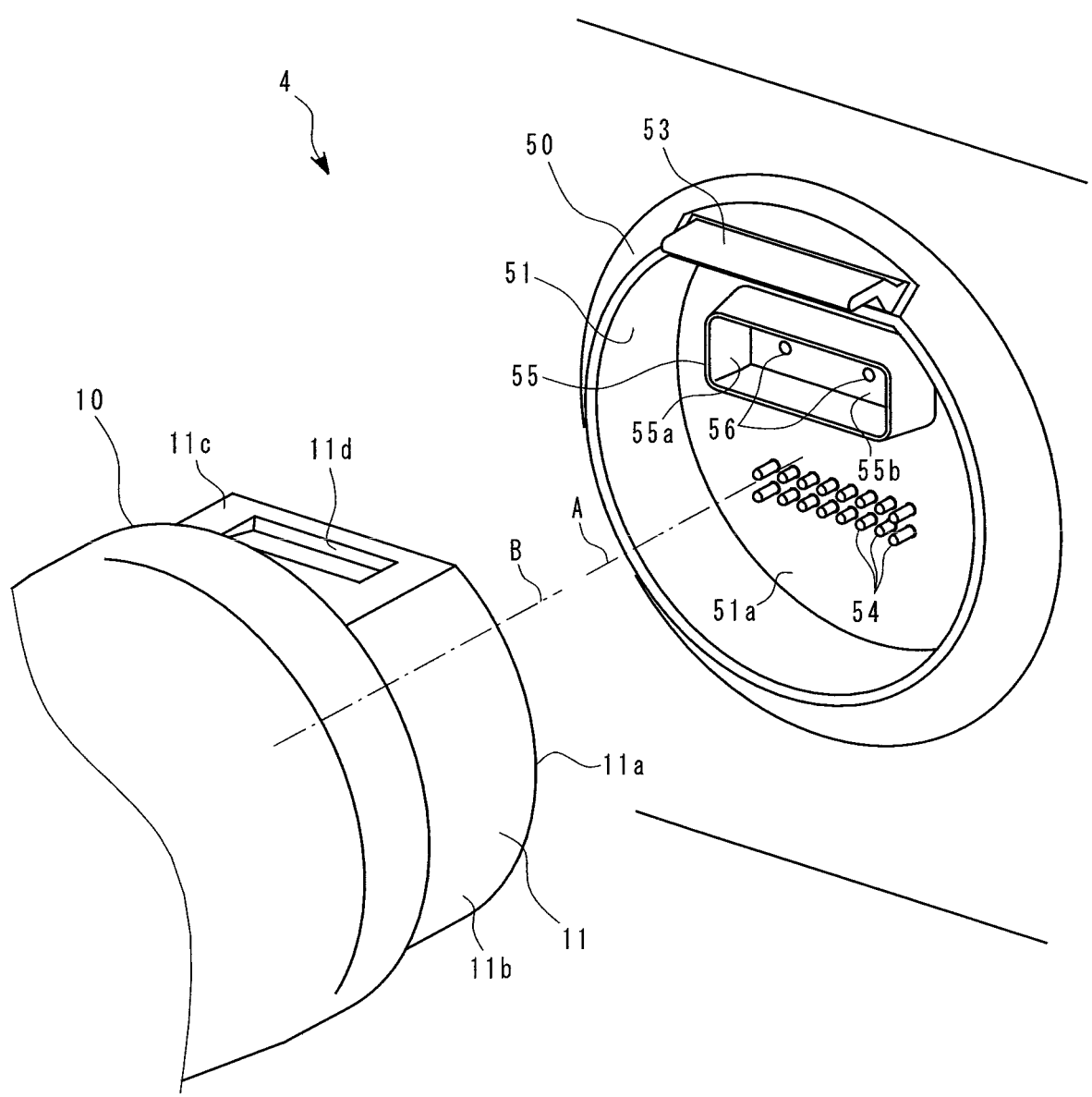
FIG. 2 is a perspective view showing the connector in a separated state.

In general, w % ben an endoscope is in use, heat generated by a light source apparatus is transferred to a plug of the endoscope, which causes an increase in a temperature of a part of an optical waveguide, in particular, in the vicinity of the part where illumination light is incident. Therefore, when pulling out the plug from the receptacle immediately after the use of the endoscope, a user has to handle the endoscope while preventing a high temperature part of the plug from contacting other components. As a result, handling of the endoscope is troublesome.

According to an embodiment to be described below, it is possible to provide a plug which enables easy handling of an endoscope immediately after the use, a connector, an endoscope apparatus, and an endoscope.

Hereinafter, a preferred embodiment of the present invention will be described with reference to drawings. Note that, in the drawings to be used for the description below, there is a case where a different scale size is used for each of the constituent elements in order to allow each of the constituent elements to be shown in a recognizable size in the drawings, and the present invention is not limited only to the number, shapes, ratio of a size of a certain constituent element to sizes of other constituent elements, and a relative positional relationship among the constituent elements shown in these drawings.

As shown in FIG. 1, an endoscope apparatus 100 includes an endoscope 1 as a medical instrument, and an endoscope processor 2. The endoscope 1 is, what is called, an electronic endoscope. The endoscope 1 is provided with an image pickup apparatus configured to pick up an image. The endoscope 1 and the endoscope processor 2 are connected to each other through a connector 4 to be described later.

The connector 4 includes a plug 10 provided to the endoscope 1 and a receptacle 50 provided to the endoscope processor 2. The plug 10 and the receptacle 50 are attachable to and detachable from each other. Hereinafter, a state where connection between the plug 10 and the receptacle 50 is established in the connector 4 is referred to as a connected state. Furthermore, a state where the plug 10 and the receptacle 50 are separated from each other is referred to as a separated state.

The endoscope 1 includes the plug 10, one or a plurality of optical waveguides 20, and an electric circuit 30. Since the configuration of the electronic endoscope is known, detailed description thereof will be omitted. The endoscope 1 includes an insertion portion configured to be insertable into a human body, a structure, and the like. The insertion portion of the endoscope 1 may be configured to be bending deformable or bending non-deformable.

The endoscope 1 includes one or a plurality of image pickup apparatuses configured to pick up an image through an observation window provided on the insertion portion. The image pickup apparatus includes an image sensor, and an objective lens that forms an object image on a light-receiving surface of the image sensor. The image sensor is also referred to as an imager or an image pickup device.

The electric circuit 30 includes an electric circuit that constitutes the image pickup apparatus. In other words, the electric circuit 30 includes an image sensor. Although not shown, in the present embodiment, the electric circuit 30 includes a storage element that stores characteristic information on the variation in color of the image sensor. Note that the number and the configuration of the electric circuit 30 included in the endoscope 1 are not specifically limited. The electric circuit 30 may include, for example, an electric switch that is operated by the user. The electric circuit 30 is electrically connected to an electric circuit 2b provided in the endoscope processor 2, when the connector 4 is in the connected state.

In addition, the insertion portion of the endoscope 1 is provided with an illumination window through which illumination light for illuminating an object of the image pickup apparatus is emitted. The illumination light is emitted from a light source apparatus 2a provided in the endoscope processor 2. The illumination light emitted from the light source apparatus 2a is transmitted to the illumination window via the optical waveguide 20, when the connector 4 is in the connected state.

Figure 3:
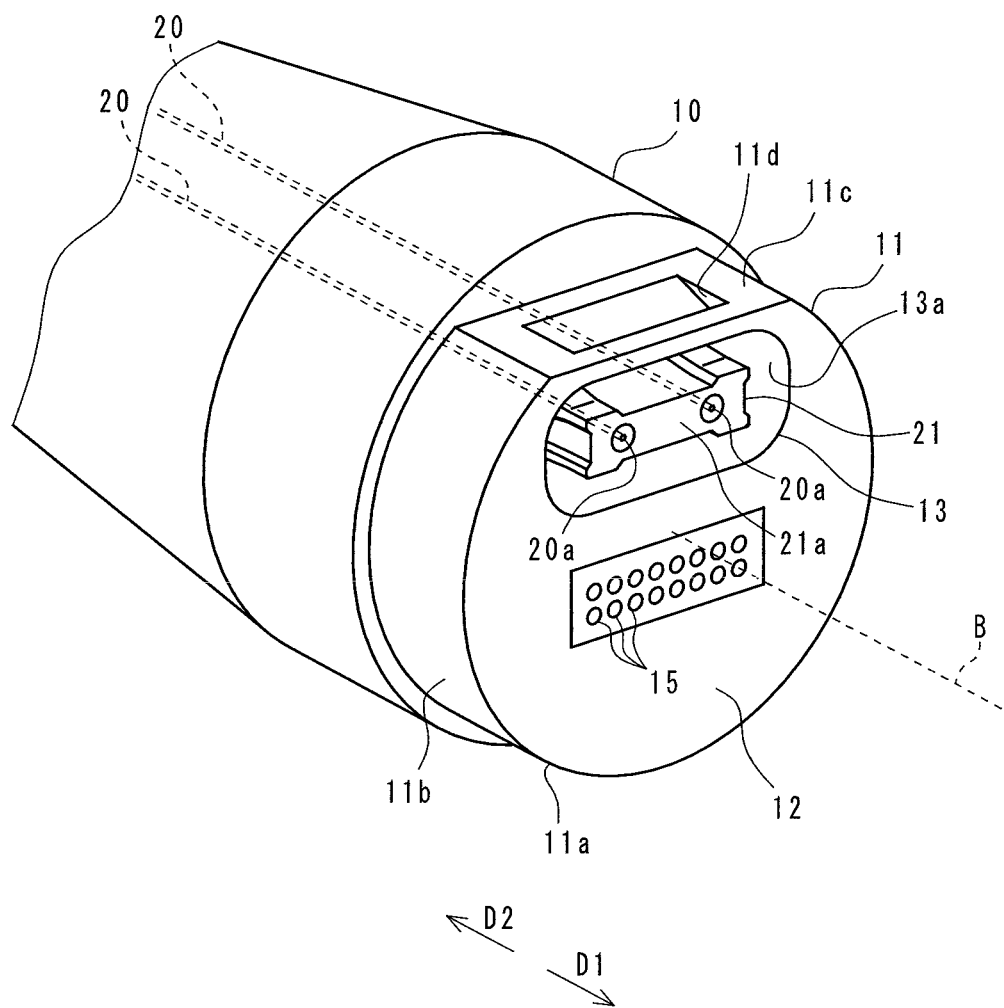
FIG. 3 is a perspective view showing a connecting surface of a plug.

In the present embodiment, as one example, the endoscope 1 includes two optical waveguides 20. The optical waveguides 20 are optical fibers, as one example, in the present embodiment. As described later, one end face 20a of each of the optical waveguides 20 is exposed in the plug 10, as shown in FIG. 3. The end faces 20a of the optical waveguides 20 are held at positions where the illumination light emitted from the light source apparatus 2a is incident on the optical waveguides 20, when the connector 4 is in the connected state. Note that as long as each of the optical waveguides 20 is configured to transmit the light incident on the end face 20a to the illumination window, the configuration of the optical waveguides 20 is not limited to the optical fibers. The optical waveguides 20 may be relay lenses, for example.

The endoscope processor 2 includes the receptacle 50, the light source apparatus 2a, and the electric circuit 2b. The power for driving the endoscope processor 2 may be supplied from outside, such as a commercial power source, or may be supplied from a battery provided in the endoscope processor 2.

The light source apparatus 2a includes a light source 2c configured to emit light. The type of the light source 2c is not specifically limited. In the present embodiment, as one example, the light source 2c is an LED. Note that the light source 2c may be a laser diode, a halogen lamp, or the like. The light source apparatus 2a may include optical elements such as a lens, a prism, a mirror, a filter, and the like.

The electric circuit 2b is configured to communicate with the electric circuit 30 provided in the endoscope 1 and supply power to the electric circuit 30, when the connector 4 is in the connected state. The electric circuit 2b includes an image processing apparatus. The image processing apparatus is configured to process a video signal outputted from the image pickup apparatus provided in the endoscope 1 and convert the video signal into a signal that can be displayed on an image display apparatus, not shown.

In addition, the image processing apparatus corrects variation in color of an image to be displayed on the image display apparatus, based on the characteristic information on the variation in color of the image sensor. The characteristic information is stored in the storage element of the electric circuit 30. The correction of the variation in color is generally called as white balance correction.

Next, description will be made on a detailed configuration of the connector 4. As described above, the connector 4 includes the plug 10 provided to the endoscope 1 and the receptacle 50 provided to the endoscope processor 2.

Figure 11:
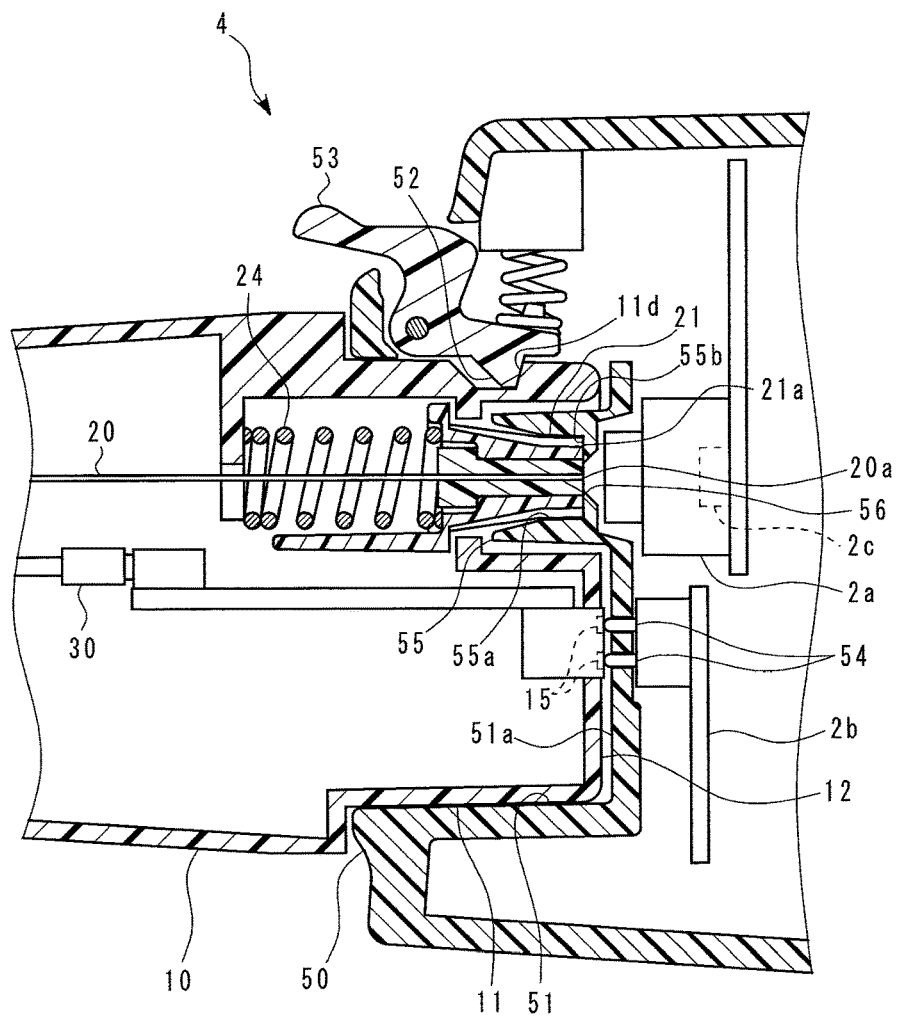
FIG. 11 is a view showing the plug and the receptacle that are in a connected state in the cross sections in FIG. 5 and FIG. 8.

As shown in FIGS. 2, 4, 5, and 6, the receptacle 50 includes a recessed portion 51. The plug 10 shown in FIGS. 2, 3, 7, 8, and 9 includes a coupling portion 11 having a columnar shape. The coupling portion 11 is configured to be insertable into the recessed portion 51. FIG. 11 shows the connected state in which the coupling portion 11 is inserted into the recessed portion 51.

The recessed portion 51 is open on an outer surface of the endoscope processor 2, with a direction along a predetermined linear first axis A as a depth direction. The coupling portion 11 can be inserted into the recessed portion 51 from a distal end 11a side, along the predetermined first axis A fixed in the recessed portion 51. The recessed portion 51 includes a bottom surface 51a having a planar shape orthogonal to the first axis A.

When the connector 4 is in the connected state, the coupling portion 11 is inserted into the recessed portion 51 to a predetermined depth. A connecting surface 12 having a planar shape is formed at the distal end 11a of the coupling portion 11. The connecting surface 12 is opposed to the bottom surface 51a of the recessed portion 51, when the connector 4 is in the connected state.

In the description below, a linear axis, which is along the insertion direction of the coupling portion 11 formed in the columnar shape into the recessed portion 51, is referred to as a second axis B. Note that the second axis B is a virtual axis fixed in the plug 10. When the connector 4 is in the connected state, the first axis A and the second axis B are substantially parallel to each other. In addition, in the description below, in the plug 10, the direction toward the distal end 11a of the coupling portion 11 along the second axis B is referred to as a first direction D1, and the direction opposite to the first direction D1 is referred to as a second direction D2. The first direction D1 at the time when the connector 4 is transitioned from the separated state to the connected state is the direction in which the coupling portion 11 of the plug 10 is inserted into the receptacle 50. The first direction D1 in the connected state is a direction in which the plug 10 faces the bottom surface 51a of the receptacle 50 along the second axis B which is a linear axis. In the present embodiment, the connecting surface 12 has a planar shape orthogonal to the second axis B.

The recessed portion 51 and the coupling portion 11 are a hole and a spindle that are in a relation of, what is called, loose fit. In other words, the recessed portion 51 and the coupling portion 11 are fitted to each other, with a predetermined gap therebetween. The spindle, here, has a shaft shape or a bar shape, for example, and is a member having an outer shape configured to be fitted into the hole. In addition, the recessed portion 51 and the coupling portion 11 are configured such that the relative rotation therebetween around the axis is restricted in a state where the recessed portion 51 and the coupling portion 11 are fitted to each other.

Figure 4:
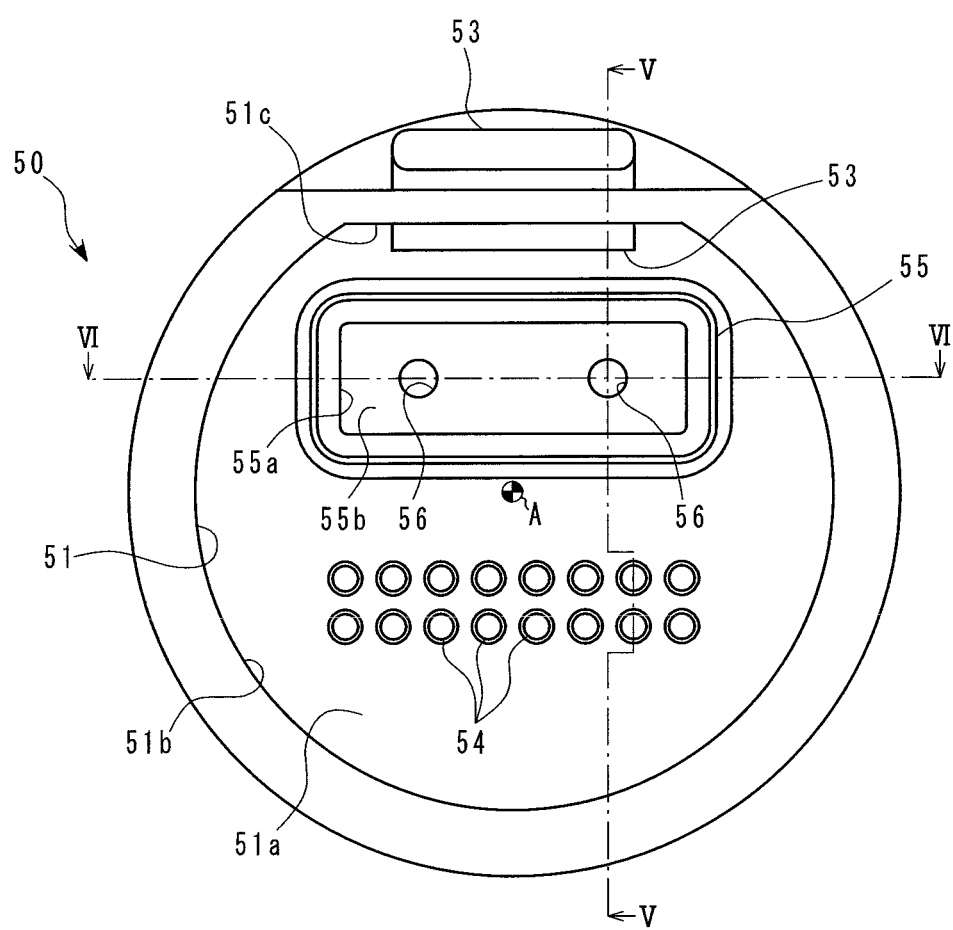
FIG. 4 is a view of a receptacle viewed from a direction of an opening.
Figure 5:
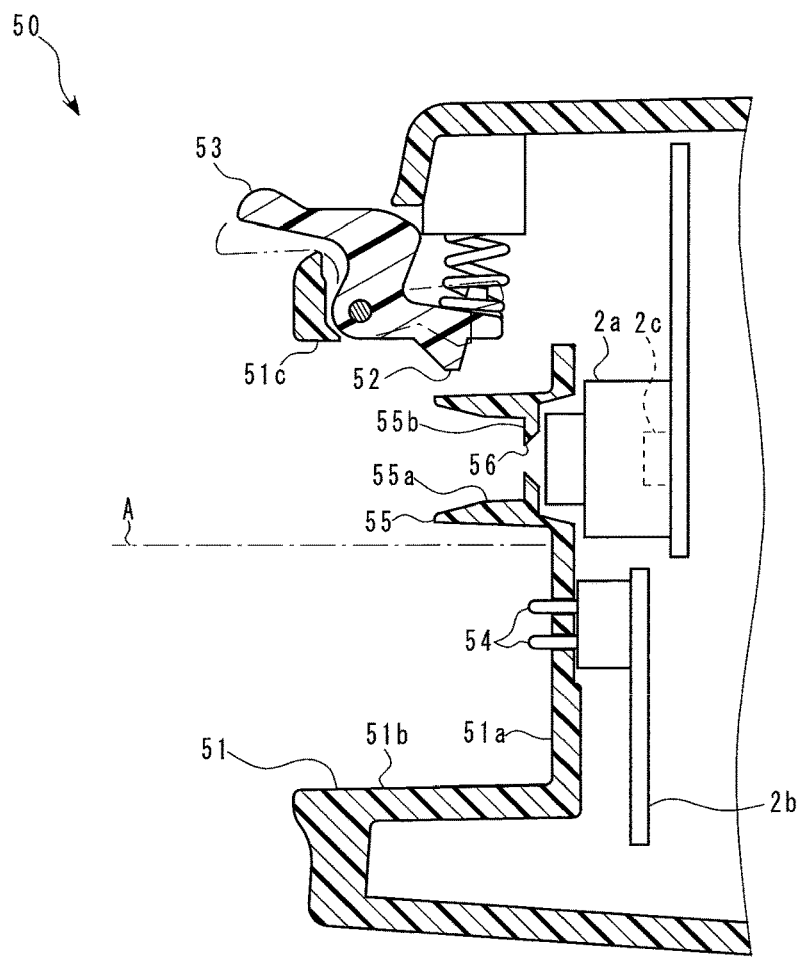
FIG. 5 is a sectional view taken along the line V-V in FIG. 4.
Figure 6:
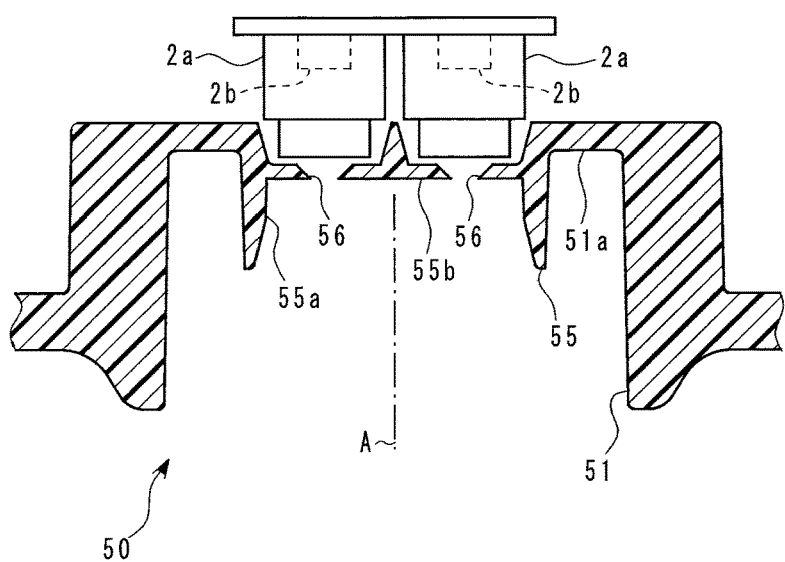
FIG. 6 is a sectional view taken along the line VI-VI in FIG. 4.

Specifically, as shown in FIG. 4, the recessed portion 51 is a hole having a D-shape when viewed from the direction parallel to the first axis A. The D-shaped hole is a hole having a plane portion 51c provided at a part of a cylindrical surface 51b of the circular hole, with the first axis A as a center axis, when viewed from the direction parallel to the first axis A. The plane portion 51c is nearly parallel to and separated from the first axis A. The distance between the first axis A and the plane portion 51c is smaller than a radius of the cylindrical surface 51b. Note that, as one example in the present embodiment, the inner peripheral surface of the recessed portion 51 has a tapered shape in which the diameter decreases toward the bottom surface 51a along the first axis A.

Figure 7:
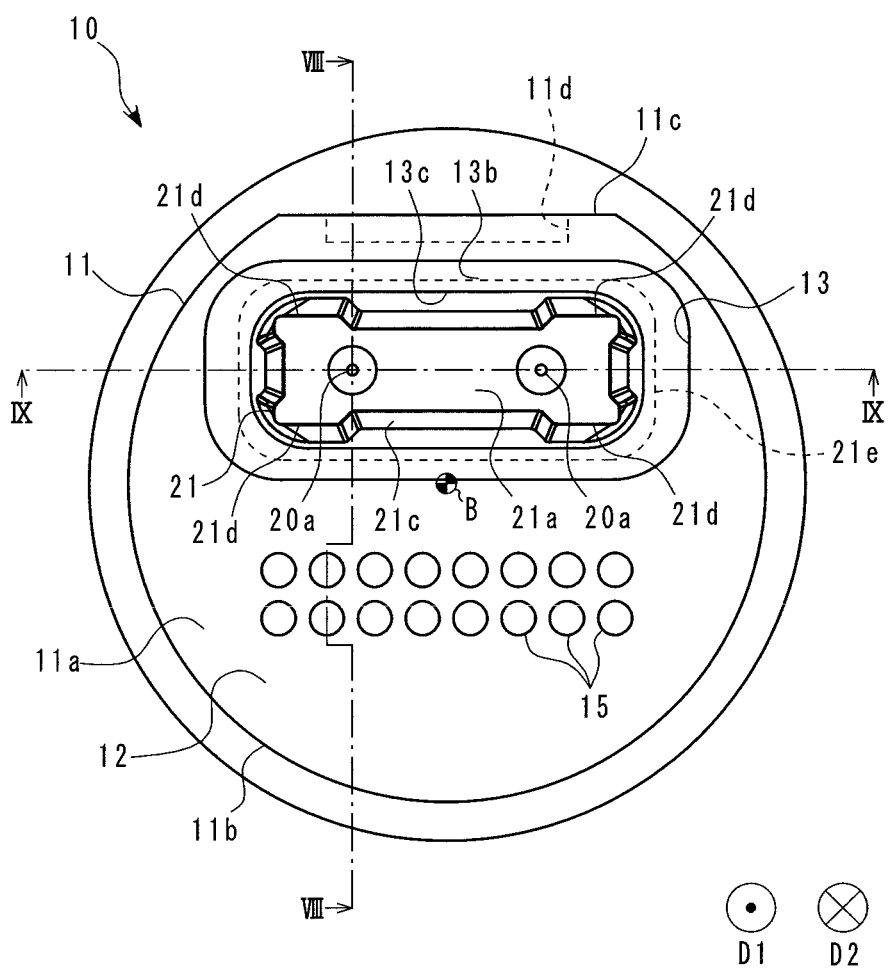
FIG. 7 is a view of the plug viewed from a first direction.
Figure 8:
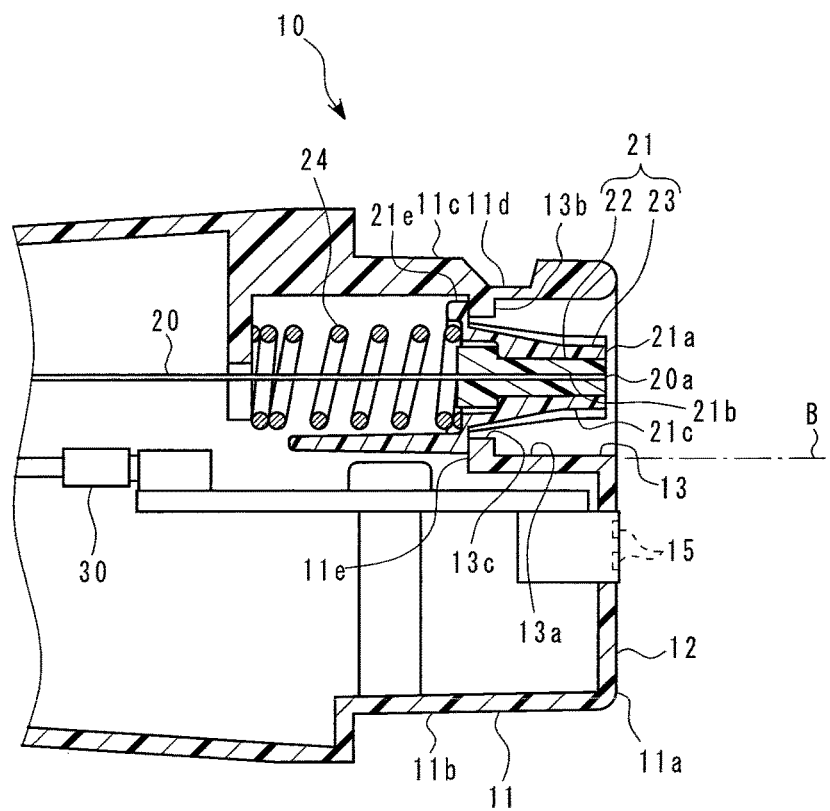
FIG. 8 is a sectional view taken along the line VIII-VIII in FIG. 7.
Figure 9:
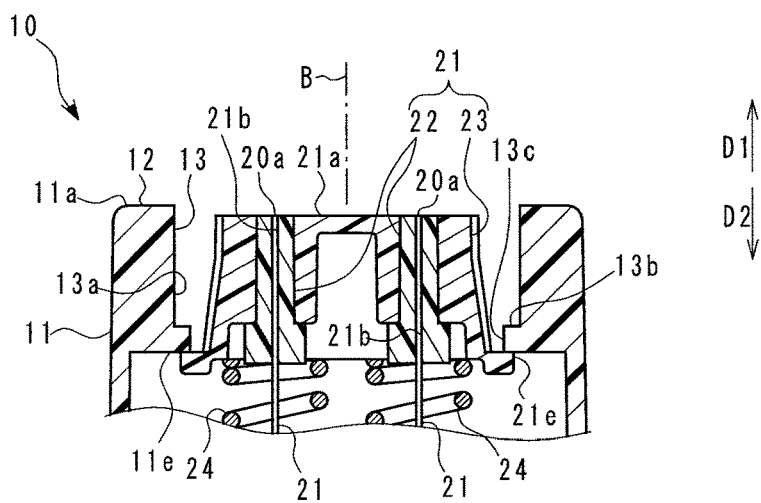
FIG. 9 is a sectional view taken along the line IX-IX in FIG. 7.

Furthermore, as shown in FIG. 7, the coupling portion 11 is a spindle having a D-shape which is substantially analogous to the inner peripheral shape of the recessed portion 51, when viewed from the direction parallel to the second axis B. The D-shaped spindle is a spindle having a plane portion 11c at a part of a cylindrical surface 11b, with the second axis B as a center axis, when viewed from the direction parallel to the second axis B. The plane portion 11c is nearly parallel to and separated from the second axis B. The distance between the second axis B and the plane portion 11c is smaller than the radius of the cylindrical surface 11b. Note that, as one example in the present embodiment, an outer peripheral surface of the coupling portion 11 has a tapered shape in which the diameter decreases toward the distal end 11a along the second axis B.

In the separated state of the connector 4, when inserting the plug 10 into the receptacle 50, the user visually identifies the plane portion 11c of the coupling portion 11, to match the direction of the plane portion 11c with the direction of the plane portion 51c of the recessed portion 51, to thereby be capable of determining the attitude of the plug 10 in the rotation direction around the second axis B.

In the connected state, the plane portion 51c of the recessed portion 51 and the plane portion 11c of the coupling portion 11 are opposed to each other. Note that the configuration for restricting the relative rotation between the recessed portion 51 and the coupling portion 11 is not limited to the one disclosed in the present embodiment. For example, the configuration for restricting the relative rotation between the recessed portion 51 and the coupling portion 11 may be achieved by configuring the recessed portion 51 and the coupling portion 11 as a hole and a spindle that have a non-circular shape such as a rectangular shape, a polygonal shape, or the like.

The receptacle 50 includes an engaging claw 52, a release lever 53, a plurality of connection pins 54, a guide portion 55, and one or a plurality of emission holes 56. The plug 10 includes an engaging hole 11d, a plurality of electric contacts 15, a hole portion 13, and a holding portion 21.

The engaging claw 52 protrudes from the inner peripheral surface of the recessed portion 51 toward the radially inward direction, and is configured to engage with the coupling portion 11 in the connected state. The engaging claw 52 is configured to restrict the movement of the coupling portion 11 in the direction (second direction D2) in which the coupling portion 11 gets out from the recessed portion 51, in the connected state. In other words, the engaging claw 52 prevents the plug 10 from falling off from the receptacle 50 in the connector 4 that is in the connected state.

In the present embodiment, as one example, the engaging claw 52 protrudes from the plane portion 51c of the recessed portion 51 in a direction approaching the first axis A. On the other hand, the engaging hole 11d having a recessed shape is formed on the plane portion 11c of the coupling portion 11. The engaging claw 52 is fitted in the engaging hole 11d in the connected state.

The engaging claw 52 releases the engagement with the coupling portion 11 according to the movement of the release lever 53. In the present embodiment, the engaging claw 52 is biased in the direction approaching the first axis A by a spring, etc. Therefore, in a case where a force is not applied to the release lever 53 by the user in the connected state, the engaging claw 52 is maintained in the state engaged with the engaging hole 11d. Then, in a case where a force is applied to the release lever 53 by the user in the connected state, the engaging claw 52 moves in the direction away from the first axis A, to thereby cause the state engaged with the engaging hole 11d to be released. In the structure for preventing the plug 10 from falling off from the receptacle 50, the release lever 53 with which the user performs operation for releasing the engagement between the engagement claw 52 and the engaging hole 11d may be provided on the plug 10 side.

With the fitting between the coupling portion 11 and recessed portion 51 and the engagement between the engaging hole 11d and the engaging claw 52, as described above, the coupling portion 11 of the plug 10 is held at a predetermined position in the recessed portion 51 of the receptacle 50, in the connected state.

Next, description will be made on a configuration for electrically connecting the plug 10 and the receptacle 50.

The plurality of electric contacts 15 are disposed, in an exposed state, on the connecting surface 12 of the coupling portion 11 of the plug 10. The plurality of electric contacts 15 are electrically connected to the electric circuit 30 of the endoscope 1. The surface of each of the electric contacts 15 has a planar shape substantially parallel to the connecting surface 12.

On the other hand, the plurality of connection pins 54 are disposed on the bottom surface 51a of the recessed portion 51 of the receptacle 50. The plurality of connection pins 54 are electrically connected to the electric circuit 2b of the endoscope processor 2. Each of the connection pins 54 protrudes from the bottom surface 51a in parallel with the first axis A toward the direction of the opening of the recessed portion 51. Each of the connection pins 54 extends and contracts in the direction parallel to the first axis A. The connection pins 54 are the ones generally called as pogo pins, spring pins, and the like.

The plurality of connection pins 54 are arranged at the positions in contact respectively with the plurality of electric contacts 15 of the plug 10, in the connected state. Positioning of the plurality of electric contacts 15 and the plurality of connection pins 54 is performed with the above-described fitting between the coupling portion 11 and the recessed portion 51 and the engagement between the engaging hole 11d and the engaging claw 52.

The plurality of electric contacts 15 of the plug 10 are brought in contact respectively with the plurality of connection pins 54 of the receptacle 50, to thereby achieve the electrical connection between the electric circuit 30 of the endoscope 1 and the electric circuit 2b of the endoscope processor 2.

In the present embodiment, in the separated state, among the plurality of connection pins 54, one or a plurality of power source pins and one or a plurality of grounding pins protrude further in the direction of the opening of the recessed portion 51 than other pins. The power source pin is electrically connected to a predetermined potential of the power source circuit in the electric circuit 2b. In addition, the grounding pin is electrically connected to a grounding potential. In other words, the power source pin and the grounding pin are for supplying power from the electric circuit 2b to the electric circuit 30 of the endoscope 1. In addition, among the plurality of connection pins 54, the other pins except for the power source pin and the grounding pin are for performing communication between the electric circuit 2b and the electric circuit 30 of the endoscope 1.

In the separated state, when the plug 10 is inserted into the receptacle 50, among the plurality of connection pins 54, the power source pin and the grounding pin are electrically connected to the electric circuit 30 of the endoscope 1 before the other pins. In other words, when the plug 10 is inserted into the receptacle 50, power is supplied to the electric circuit 30, and thereafter communication between the electric circuit 2b and the electric circuit 30 is established. In addition, in the connected state, when the plug 10 is pulled out from the receptacle 50, the communication between the electric circuit 2b and the electric circuit 30 is canceled, and thereafter the power supply to the electric circuit 30 is cut off.

Thus, when the plug 10 is inserted, the power supply to the electric circuit 30 of the endoscope 1 is established before the establishment of the communication, and when the plug 10 is pulled out, the communication is blocked before stopping the power supply to the electric circuit 30 of the endoscope 1, to thereby prevent breakage of the electric circuit 30 and enable the electric circuit 30 to surely operate even if the plug 10 is inserted and extracted while the power source of the endoscope processor 2 is on.

Next, description will be made on the configuration in which one or a plurality of optical waveguides 20 are connected between the plug 10 and the receptacle 50.

Here, the connection of each optical waveguide 20 means that the end face 20a of the optical waveguide 20 as an optical fiber is held on a predetermined optical path. Specifically, the connection of the optical waveguide 20 in the present embodiment means that the end face 20a of the optical waveguide 20 disposed on the plug 10 side is held at the position where the end face 20a receives incidence of the illumination light emitted from the light source apparatus 2a.

Description is made first on the connection of the optical waveguide 20 in the plug 10.

In the plug 10, one or a plurality of optical waveguides 20 are held by the holding portion 21. The holding portion 21 holds the one or the plurality of optical waveguides 20 such that the end face 20a of each of the one or the plurality of optical waveguides 20 is directed in the first direction D1.

The end face 20a of each of the one or the plurality of optical waveguides 20 is disposed on the second direction D2 side with respect to the connecting surface 12. In other words, the distal end 11a of the coupling portion 11 of the plug 10 protrudes to the distal end side (in first direction D1) with respect to the end face 20a of each of the one or the plurality of optical waveguides 20.

In the present embodiment, as one example, the endoscope 1 includes two optical waveguides 20, and one holding portion 21 configured to hold the two optical waveguides 20.

The holding portion 21 is disposed in the hole portion 13 having a recessed shape. The hole portion 13 is open on the connecting surface 12. As described above, the connecting surface 12 is a plane orthogonal to the second axis B. The hole portion 13 is a hole that is open on the connecting surface 12 and has the depth direction in the second direction D2.

The holding portion 21 has a pillar shape that extends along the second axis B. The holding portion 21 protrudes from the bottom surface 13b of the hole portion 13 toward the first direction D1. The surface of the holding portion 21, which is located at the end in the first direction D1, is referred to as a distal end surface 21a. The distal end surface 21a of the holding portion 21 is a plane orthogonal to the second axis B. The distal end surface 21a is exposed in the first direction D1 in the plug 10.

The holding portion 21 is separated from the inner side surface 13a of the hole portion 13. In other words, when viewing the holding portion 21 from the first direction D1 along the second axis B, a gap is formed around the holding portion 21. The distal end surface 21a is disposed on the second direction D2 side with respect to the connecting surface 12. In other words, the distal end surface 21a is disposed on the depth side with respect to the opening of the hole portion 13.

The holding portion 21 includes two through holes 21b penetrating the holding portion 21 in parallel with the second axis B. One end of each of the through holes 21b is open on the distal end surface 21a, and the other end of each of the through holes 21b is open in an inner space of the plug 10. The inner space of the plug 10 communicates with an inner space of the endoscope 1 in which the optical waveguides 20 are inserted.

The optical waveguides 20 are inserted respectively in the through holes 21b. The optical waveguides 20 are fixed to the holding portion 21 at the positions where the end faces 20a substantially coincide with the distal end surface 21a.

The holding portion 21 includes a plurality of protruding portions 21d. Each of the plurality of protruding portions 21d protrudes from the outer peripheral surface 21c of the holding portion 21 and extends along the second axis B.

Specifically, the holding portion 21 in the present embodiment has a substantially rectangular outer shape when viewed from the first direction D1 along the second axis B. The plurality of protruding portions 21d are provided respectively at four corners of the rectangular-shaped holding portion 21. In addition, in the present embodiment, the holding portion 21 has a tapered outer shape that is more tapered toward the first direction D1. The two through holes 21b are aligned in the distal end surface 21a, so as to be along the longitudinal direction of the rectangular holding portion 21, when viewed from the first direction D1 along the second axis B.

Note that the holding portion 21 may be configured by a single member with which the one or the plurality of optical waveguides 20 are held. Alternatively, the holding portion 21 may be configured by a plurality of members with which the one or the plurality of optical waveguides 20 are held.

In the present embodiment, as one example, the holding portion 21 includes two pipe sleeves 22 and one main body portion 23. Each of the pipe sleeves 22 has a substantially cylinder shape, with the axis parallel to the second axis B as a center axis, and has one through hole 21b. In other words, the one pipe sleeve 22 holds the one optical waveguide 20. The main body portion 23 holds the two pipe sleeves 22. The main body portion 23 has an outer shape formed in a pillar shape extending along the second axis B, and includes the above-described plurality of protruding portions 21d.

In the present embodiment, the holding portion 21 is, what is called, a floating part, the relative movement of which is allowed within a predetermined range, with respect to the coupling portion 11. Although detailed description will be made later, the holding portion 21 is a floating part, which enables the end faces 20a of the two optical waveguides 20 to be held precisely at the predetermined positions, regardless of the fitted state of the coupling portion 11 and the recessed portion 51 of the receptacle 50. In addition, such a configuration can prevent the fitting between the coupling portion 11 and the recessed portion 51 and the fitting between the holding portion 21 and the guide portion 55 from being in a relation of double fitting.

Figure 10:
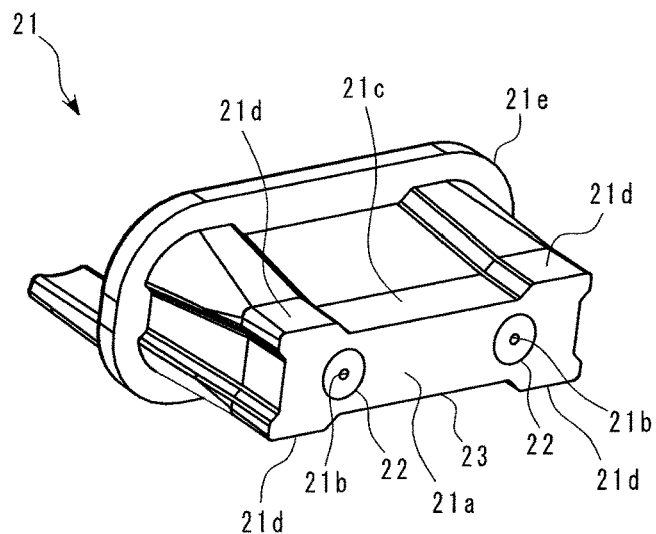
FIG. 10 is a perspective view of a holding portion as a single unit.

Description will be made on the configuration for allowing the relative movement of the holding portion 21 with respect to the coupling portion 11. The holding portion 21 and the coupling portion 11 are configured by separate and different members. FIG. 10 shows the holding portion 21 as a single unit. The coupling portion 11 includes the connecting surface 12 and the hole portion 13, as described above. A through hole 13c is formed on the bottom surface 13b of the hole portion 13. One end of the through hole 13c is open on the bottom surface 13b, and the other end of the through hole 13c is open on an inner wall surface 11e of the plug 10. The inner wall surface 11e is a plane facing in the second direction D2 and orthogonal to the second axis B.

The holding portion 21 is inserted in the through hole 13c from the second direction D2 toward the first direction D1. A gap with a predetermined width is formed between the outer peripheral surface 21c of the holding portion 21 and the through hole 13c.

A projection portion 21e is formed at the end in the second direction D2 of the outer peripheral surface 21c of the holding portion 21. The external dimension of the projection portion 21e is larger than the diameter of the through hole 13c. Furthermore, the plug 10 includes an elastic member 24 configured to bias the holding portion 21 in the first direction D1. As one example shown in the present embodiment, the elastic member 24 is a compression coil spring. The elastic member 24 may be a plate spring, a tension coil spring, or the like. In addition, the elastic member 24 may be made of rubber, urethane foam, or the like.

When an external force is not applied to the holding portion 21, the projection portion 21e is maintained in the state contacting the inner wall surface 11e by the biasing force of the elastic member 24. In the state where the projection portion 21e is in contact with the inner wall surface 11e, the distal end surface 21a of the holding portion 21 is orthogonal to the second axis B. When an external force is applied to the holding portion 21, the holding portion 21 moves with respect to the coupling portion 11. The movement of the holding portion 21 with respect to the coupling portion 11 includes not only the movement in the direction orthogonal to the second axis B but also the movement in the second direction D2, the rotation around the second axis B, and the rotation with which the tilting of the holding portion 21 with respect to the second axis B changes.

Description will be made on the configuration related to the connection of the optical waveguides 20 in the receptacle 50.

The receptacle 50 includes, inside the recessed portion 51, the guide portion 55 and the one or the plurality of emission holes 56.

The guide portion 55 protrudes from the bottom surface 51a of the recessed portion 51 in the direction of the opening along the first axis A. The guide portion 55 has a cylindrical shape and includes a hole 55a parallel to the first axis A. The hole 55a of the guide portion 55 is open in the direction of the opening of the recessed portion 51. In other words, the guide portion 55 is a projected wall portion that protrudes from the bottom surface 51a of the recessed portion 51 and disposed along the periphery of the hole 55a.

The bottom surface 55b of the hole 55a is a plane orthogonal to the first axis A. The bottom surface 55b of the hole 55a is located closer to the opening of the recessed portion 51 with respect to the bottom surface 51a of the recessed portion 51. In the present embodiment, as one example, the hole 55a has a tapered shape in which the diameter thereof decreases toward the bottom surface 55b along the first axis A.

In the connected state, the holding portion 21 of the plug 10 is fitted in the hole 55a of the guide portion 55, with a predetermined gap from the hole 55a. In addition, in the connected state, the distal end surface 21a of the holding portion 21 is in contact with the bottom surface 55b of the hole 55a.

In the connected state, the holding portion 21 is fitted in the hole 55a of the guide portion 55 and in contact with the bottom surface 55b, and thereby the holding portion 21 is positioned at the predetermined position with respect to the recessed portion 51 of the receptacle 50. In other words, the fitting of the holding portion 21 into the guide portion 55 enables the end face 20a of each of the one or the plurality of optical waveguides 20 to be positioned at the predetermined position in the receptacle 50.

The one or the plurality of emission holes 56 are formed on the bottom surface 55b of the hole 55a of the guide portion 55. The one end of each of the one or the plurality of emission holes 56 is open on the bottom surface 55b, and the other end of each of the one or the plurality of emission holes 56 is open in the inner space of the endoscope processor 2.

At the other end of each of the one or the plurality of emission holes 56, the light source apparatus 2a is disposed. The illumination light emitted from the light source apparatus 2a is incident on each of the one or the plurality of emission holes 56. In other words, the one or the plurality of emission holes 56 are windows from which the illumination light is emitted.

In the connected state, the one or the plurality of emission holes 56 are disposed at positions opposing to the end faces 20a of the optical waveguides 20. In the present embodiment, the two emission holes 56 are open on the bottom surface 55b.

In the connected state, the illumination light emitted from the light source apparatus 2a passes through the emission holes 56 to be incident on the end faces 20a of the optical waveguides 20. Thus, when the plug 10 is inserted into the receptacle 50, the guide portion 55 guides the end faces 20a of the optical waveguides 20 to the positions opposing to the emission holes 56. The end faces 20a of the optical waveguides 20 are held at the positions opposing to the emission holes 56, to thereby establish the connection of the optical waveguides 20.

As described above, in the present embodiment, the end faces 20a of the two optical waveguides 20 are held by the one holding portion 21 in the plug 10. The holding portion 21 is a floating part, the movement of which is allowed within the predetermined range, with respect to the coupling portion 11 to be inserted into the receptacle 50. Even if, in the connected state, the coupling portion 11 moves slightly with respect to the recessed portion 51, the distal end surface 21a of the holding portion 21 is maintained in the state pressed against the bottom surface 55b by the biasing force of the elastic member 24. Therefore, in the connector 4 according to the present embodiment, both of the end faces 20a of the two optical waveguides 20 can be stably held at the positions opposing to the two emission holes 56, to thereby be capable of reducing the fluctuation in the transmission efficiency of the illumination light from the light source apparatus 2a to the optical waveguides 20.

During the use of the endoscope 1, the heat generated by the light source apparatus 2a is transmitted to the end faces 20a of the two optical waveguides 20 and the distal end surface 21a of the holding portion 21, which results in a temperature rise of the end faces 20a of the two optical waveguides 20 and the holding portion 21.

In the plug 10 according to the present embodiment, the holding portion 21 is disposed in the hole portion 13 that is open on the connecting surface 12, and only the distal end surface 21a is exposed in the first direction D1. In addition, the distal end surface 21a of the holding portion 21 is located in the second direction D2, which is opposite to the first direction D1, with respect to the connecting surface 12. In other words, the periphery of the outer peripheral surface 21c of the holding portion 21 is surrounded by the inner side surface 13a of the hole portion 13 separated from the holding portion 21. The inner side surface 13a of the hole portion 13 is a part of the coupling portion 11. During the use of the endoscope, since the coupling portion 11 is separated from the light source apparatus 2a, with a space therebetween, the quantity of heat transmitted from the light source apparatus 2a to the coupling portion 11 is relatively small. In addition, the coupling portion 11 is in contact with the recessed portion 51 of the receptacle 50, which enables easy radiation of the heat. Therefore, during the use of the endoscope, the temperature of the coupling portion 11 is lower than those of the end faces 20a of the two optical waveguides 20 and the holding portion 21.

In the plug 10 according to the present embodiment, the peripheries of the holding portion 21 and the end faces 20a of the two optical waveguides 20, the temperatures of which become high after the use of the endoscope, are surrounded by the coupling portion 11, the temperature of which is low. Therefore, in the present embodiment, when the plug 10 is pulled out from the receptacle 50 after the use of the endoscope 1, it is possible to prevent the holding portion 21 and the end faces 20a of the two optical waveguides 20, the temperatures of which are high, from contacting other components.

As described above, the plug 10, the connector 4, and the endoscope apparatus 100 according to the present embodiment are capable of preventing the parts of the plug 10, the temperature of which become high from contacting other components, which enables easy handling of the endoscope immediately after the use.

The present invention is not limited to the above-described embodiment, but can be changed appropriately within a range not departing from the gist or concept of the invention that can be read from claims and throughout the specification. The plug, connector, and the endoscope apparatus with such changes are also included in the technical range of the present invention.

In the above-described embodiment, the endoscope is disclosed as an example of the medical instrument provided with the optical waveguides. However, the medical instrument is not limited to the endoscope. For example, the medical instrument may be a treatment instrument configured to emit light from a light source apparatus connected through a connector. In addition, the light emitted from the medical instrument is not limited to the light for illuminating an object of the image pickup apparatus. For example, the light emitted from the light source apparatus may be light for sterilization, heating, or the like.

What is claimed is:
1. A plug for use with a medical instrument, the plug comprising:
   at least one optical waveguide;
   a coupling portion configured to be inserted into a receptacle in a longitudinal direction of the coupling portion;

a connecting surface configured to face the receptacle in a state in which the coupling portion is inserted into the receptacle;
an opening provided on the connecting surface, the opening having a recessed shape; and
a holding portion disposed in the opening, the holding portion being configured to hold the at least one optical waveguide, an end face of the at least one optical waveguide is directed to the receptacle in the state in which the coupling portion is inserted into the receptacle,
wherein the holding portion and the end face of the at least one optical waveguide are spaced apart from the connecting surface in the longitudinal direction.

2. The plug according to claim 1, wherein the holding portion is movably disposed within the opening in the longitudinal direction.

3. The plug according to claim 1, wherein the holding portion has a pillar shape extending in the longitudinal direction, the holding portion including a plurality of protruding portions protruding from an outer peripheral surface of the holding portion and extending in the longitudinal direction.

4. The plug according to claim 1, wherein the holding portion includes at least one pipe sleeve respectively corresponding to the at least one optical waveguide, the at least one pipe sleeve having a through hole in the end face of the at least one optical waveguide is inserted, and the holding portion includes a main portion configured to hold the at least one pipe sleeve.

5. The plug according to claim 1, wherein the holding portion is separate from the coupling portion.

6. The plug according to claim 5, further comprising an elastic member configured to bias the holding portion in the longitudinal direction.

7. The plug according to claim 1, wherein an outer shape of the coupling portion has a non-circular shape.

8. The plug according to claim 1, wherein an outer shape of the coupling portion has a D-shape.

9. The plug according to claim 1, wherein the connecting surface includes a plurality of electric contacts.

10. The plug according to claim 1, wherein
the holding portion includes a distal end surface that is parallel to the connecting surface, and
the end face of the at least one optical waveguide is exposed on the distal end surface.

11. The plug according to claim 1, wherein a distal end face of the holding portion is within the opening.

12. The plug according to claim 1, wherein the end face of the one or more optical waveguide is within the opening.

13. The plug according to claim 1, wherein the at least one optical waveguide comprises two optical waveguides separate in a direction orthogonal to the longitudinal direction.

14. A connector for for use with a medical instrument, the connector comprising:
a receptacle; and
a plug, wherein the plug comprises:
a coupling portion configured to be inserted into the receptacle in a longitudinal direction of the coupling portion;
a connecting surface configured to face the receptacle in a state in which the coupling portion is inserted into the receptacle;
an opening provided on the connecting surface, the opening having a recessed shape; and
a holding portion disposed in the opening, the holding portion being configured to hold the at least one optical waveguide, an end face of the at least one optical waveguide is directed to the receptacle in the state in which the coupling portion is inserted into the receptacle,
wherein the holding portion and the end face of the at least one of optical waveguide are spaced apart from the connecting surface in the longitudinal direction, and
the receptacle includes a recessed portion in which the coupling portion is inserted.

15. The connector according to claim 14, wherein the receptacle includes:
a guide portion including a hole in which the holding portion is fitted in a state in which the coupling portion is inserted into the recessed portion; and
at least one emission hole formed in the hole at a position opposing the end face of the at least one optical waveguide in the state in which the holding portion is inserted into the receptacle.

16. An endoscope apparatus comprising:
an endoscope comprising a plug, and
an endoscope processor comprising a receptacle and a light source,
wherein the plug comprising:
at least one optical waveguide;
a coupling portion configured to be inserted into the receptacle in a longitudinal direction of the coupling portion;
a connecting surface configured to face the receptacle in a state in which the coupling portion is inserted into the receptacle;
an opening provided on the connecting surface, the opening having a recessed shape; and
a holding portion disposed in the opening, the holding portion being configured to hold the at least one optical waveguide, an end face of the at least one optical waveguide is directed to the receptacle in the state in which the coupling is inserted into the receptacle,
wherein the holding portion and the end face of the at least one optical waveguide are spaced apart from the connecting surface in the longitudinal direction, and
the receptacle comprising:
a recessed portion in which the coupling portion is inserted; and
one or a plurality of emission holes, each being formed at a position opposing to the end face of the at least one optical waveguide in the state in which the coupling portion is inserted into the receptacle; and
the light source configured to emit light toward the at least one emission hole in the state where the coupling portion is inserted into the receptacle.

17. The plug according to claim 16, wherein a distal end face of the holding portion is within the opening.

18. The plug according to claim 16, wherein the end face of the one or more optical waveguide is within the opening.

19. The plug according to claim 16, wherein the at least one optical waveguide comprises two optical waveguides separate in a direction orthogonal to the longitudinal direction.

20. An endoscope comprising:
a plug of a connector for connecting at least one optical waveguide,
the plug comprising:
a coupling portion configured to be inserted into a receptacle of the connector in a longitudinal direction of the coupling portion;

a connecting surface configured to face the receptacle in a state in which the coupling portion is inserted into the receptacle;

an opening provided on the connecting surface, the opening having a recessed shape; and a holding portion disposed in the opening, the holding portion being configured to hold the at least one optical waveguide, an end face of the at least one optical waveguide is directed to the receptacle in the state in which the coupling is inserted into the receptacle, wherein the holding portion and the end face of the at least one optical waveguide are spaced apart from the connecting surface in the longitudinal direction.

* * * * *